United States Patent
Thomas et al.

(10) Patent No.: US 6,855,424 B1
(45) Date of Patent: Feb. 15, 2005

(54) BREATHABLE COMPOSITE ELASTIC MATERIAL HAVING A CELLULAR ELASTOMERIC FILM LAYER AND METHOD OF MAKING SAME

(75) Inventors: Oomman Painumoottil Thomas, Alpharetta, GA (US); Michael Allen Daley, Alpharetta, GA (US); James Russell Fitts, Jr., Gainesville, GA (US); Steven D. Flack, Marletta, GA (US); Jason Asher Bernstein, Roswell, GA (US)

(73) Assignee: Kinberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/474,043

(22) Filed: Dec. 28, 1999

Related U.S. Application Data
(60) Provisional application No. 60/113,908, filed on Dec. 28, 1998.

(51) Int. Cl.$^7$ .............................. B32B 5/24; D02G 3/32
(52) U.S. Cl. .................... 428/376; 428/131; 428/304.4; 428/315.9; 428/315.5; 428/392; 428/394; 428/375; 424/443; 424/445; 424/447; 264/51; 442/328; 442/370; 442/394
(58) Field of Search .............................. 428/131, 304.4, 428/315.9, 315.5, 392, 394, 375, 376; 264/51; 424/443, 445, 447; 442/328, 370, 39.4

(56) References Cited

U.S. PATENT DOCUMENTS

| | | | |
|---|---|---|---|
| 3,634,184 A | 1/1972 | Wang | 161/83 |
| 3,836,423 A | 9/1974 | Wagner et al. | 161/159 |
| 4,265,972 A | * 5/1981 | Rudner | 428/392 |
| 4,333,898 A | 6/1982 | Schmidtchen | 264/45.9 |
| 4,414,970 A | 11/1983 | Berry | 128/156 |
| 4,501,711 A | 2/1985 | Senuma et al. | 264/54 |
| 4,715,912 A | 12/1987 | Tillotson | 156/79 |
| 4,764,535 A | 8/1988 | Leicht | 521/51 |
| 4,867,150 A | 9/1989 | Gilbert | 128/155 |

(List continued on next page.)

FOREIGN PATENT DOCUMENTS

| | | | |
|---|---|---|---|
| EP | 0274752 | 7/1988 | ........... A41B/13/02 |
| EP | 0329411 | 8/1989 | ............. B32B/5/18 |
| EP | 0488038 | 6/1992 | ........... B32B/27/08 |
| GB | 08852940 | 11/1960 | |
| JP | 49112964 A | 10/1974 | |
| JP | 69017593 B | 3/1995 | |
| WO | 9611236 | 4/1996 | ........... C08L/53/02 |
| WO | 9856240 | 12/1998 | ............ A01J/21/02 |

Primary Examiner—William P. Watkins, III
(74) Attorney, Agent, or Firm—Jason A. Bernstein; Powell Goldstein LLP

(57) ABSTRACT

A material and method for providing a laminate of at least two layers to provide breathability and moisture barrier properties without appreciably reducing elastic properties. A first material comprises a woven or nonwoven web and a second material comprises a cellular elastomer film or fiber. Such materials may be integrated into a laminate by forming said first material onto said second material, or by joining the two materials through chemical or physical means such as the use of adhesives. The second material can be prepared by mixing a cell opening agent with the elastomeric polymer resin and extruding the mixture at appropriate conditions whereby the cell opening agent decomposes or reacts to release a gas that forms cells in the elastomer film. The material is useful in personal care products such as diapers, feminine care products, child care products, incontinence products and health care products where such properties are desirable for attributes such as comfort, body shaping, conformance, dryness and the like.

28 Claims, 5 Drawing Sheets

U.S. PATENT DOCUMENTS

| | | | |
|---|---|---|---|
| 4,898,760 A | * 2/1990 | Halberstadt et al. | 428/122 |
| 4,908,260 A | 3/1990 | Dodia et al. | 428/215 |
| 5,257,923 A | 11/1993 | Kagawa | 425/290 |
| 5,262,444 A | 11/1993 | Rusincovitch et al. | 521/50.5 |
| 5,336,554 A | 8/1994 | Knight | 428/230 |
| 5,415,538 A | 5/1995 | Kagawa | 425/174.4 |
| 5,422,172 A | 6/1995 | Wu | 428/230 |
| 5,458,951 A | 10/1995 | Kagawa | 428/155 |
| 5,476,712 A | 12/1995 | Hartman et al. | 428/317.3 |
| 5,492,741 A | 2/1996 | Akao et al. | 428/35.2 |
| 5,514,470 A | 5/1996 | Haffner et al. | 428/246 |
| 5,540,976 A | 7/1996 | Shawver et al. | 428/198 |
| 5,571,529 A | * 11/1996 | Cheong | 424/445 |
| 5,593,395 A | 1/1997 | Martz | 604/304 |
| 5,593,632 A | 1/1997 | Kagawa | 264/284 |
| 5,634,216 A | 6/1997 | Wu | 2/239 |
| 5,648,107 A | 7/1997 | Kagawa et al. | 425/363 |
| 5,786,412 A | 7/1998 | Shah et al. | 524/264 |
| 5,840,632 A | 11/1998 | Miller | 442/62 |
| 5,904,970 A | * 5/1999 | Lauer et al. | 428/71 |
| 5,932,497 A | * 8/1999 | Morman et al. | 442/286 |
| 5,938,874 A | * 8/1999 | Palomo et al. | 156/73.1 |
| 5,939,464 A | * 8/1999 | Wang | 521/139 |
| 6,074,966 A | * 6/2000 | Zlatkus | 442/413 |

* cited by examiner

BREATHABLE COMPOSITE ELASTIC MATERIAL HAVING A CELLULAR ELASTOMERIC FILM LAYER AND METHOD OF MAKING SAME

CROSS-REFERENCE TO RELATED APPLICATION

This application claims priority from U.S. Provisional Patent Application Ser. No. 60/113,908, filed Dec. 28, 1998, and commonly assigned to the assignee of the present invention, the disclosure of which is incorporated by reference herein in its entirety.

FIELD OF THE INVENTION

The present invention relates to breathable elastomeric films and laminate materials comprised of at least one layer of a woven or nonwoven material and at least one layer of an elastomer film or fibrous material having open and/or closed cells formed therein by a cell opening agent.

BACKGROUND OF THE INVENTION

Materials that have desirable breathability and moisture barrier properties are useful in personal care products such as diapers, incontinence and feminine care articles, where the object is to contain fluids within the product structure while allowing for external air exchange. A traditional means for providing such materials is to incorporate an outer cover having a breathable microporous structure yet which is capable of maintaining liquid barrier properties. These materials typically comprise a laminate or composite of a film layer and an elastic layer (usually made of a nonwoven material). Traditionally, the film layer has been made of a polyolefin or polyurethane material. However, such materials have been limited because they did not provide suitable elastic and breathability properties required for personal care products. Recently, some extensible polyolefins have been developed, but such materials have limited elasticity.

Aperturing polyolefins or similar materials can be done by mechanical or other force applying techniques. Mechanical aperturing tends to create ragged edge holes, whereas blowing agents tend to create smoother holes. Smoother holes are stronger and are more resist to tearing than are ragged edge holes because there are fewer stress points in the film. Mechanical aperturing of polyolefins is possible because the film formed therefrom has sufficient stiffness to prevent substantial deformation of the sheet when a pin or other aperturing force is passed therethrough. For materials such as elastomers that form sheets of greater flexibility than polyolefins, mechanical aperturing has been problematic because the material deforms excessively when punctured, resulting in holes that have poor quality and definition or a material that has compromised mechanical properties.

Breathability can also be achieved by the formation of holes or cells within a film. One method by which this can be achieved is by introducing particles of a material such as calcium carbonate into the extrusion mix. The extruded film encapsulates or forms cells or pockets around the particles. When the film is stretched the pockets elongate to form microholes and/or microtears, through which air can pass. A problem with this technique is that hole definition can be poor because stress is introduced into the microporous area, and, if the particles are irregular in shape, the micropores formed can be of irregular shape and subject to tearing, thereby reducing strength. This technique may not be practicable for forming micropores in materials, such as certain elastomers. Even if micropores could be regularly formed in these materials, conceivably they would collapse or close due to retraction of the polymer when the biasing force or stress is removed.

Elastomers are desirable materials for use in personal care products because their stretch and recovery attributes lend themselves to improved shaping, conformability, and potentially improved functionality, compared to polyolefins. Introducing holes or openings in the form of pores or apertures in elastomers, however, has been a problem because it is difficult to retain the porous structure due to relaxation of the elastomer. It would be desirable to have a process that could form apertures in elastomers and provide predictable aperture definition without appreciably increasing manufacturing cost. It would also be desirable for such an aperturing process to allow for control of hole size, hole distribution and other related properties as a function of stretch or elongation.

Accordingly, it is an object of the present invention to provide a cellular elastomeric composite material which provides an appropriate level of breathability, fluid barrier properties, and elasticity suitable for use in personal care products.

It is yet another object of the present invention to provide a process for forming a cellular elastomer film composite having predictable hole definition, hole distribution and acceptable mechanical properties.

It is a further object of the present invention to provide a composite laminate material comprised of at least one layer of a woven or nonwoven material and a layer of a cellular elastomer film or fibrous material which has pores that are created by adding a cell opening agent to an elastomer polymer and extruding the mixture so that the cell opening agent forms open and/or closed cells in the film produced from the elastomer polymer.

It is yet another object of the present invention to provide a material having a breathable film layer suitable for use as a stretchable top sheet for use in management of body fluids such as menses, blood, urine and runny bowel movement.

SUMMARY OF THE INVENTION

The present invention provides materials and methods for forming a laminate of at least two layers to provide breathability and moisture barrier properties without appreciably reducing elastic properties. A first material comprises a woven or nonwoven web and a second material comprises an elastomer film or fiber. Such materials may be integrated into a laminate by forming the first material onto the second material, or by joining the two materials through chemical or physical means such as the use of adhesives. The second material can be prepared by mixing a cell opening agent with the elastomeric polymer resin and extruding the mixture at appropriate conditions whereby the cell opening agent decomposes to release a gas that forms open and/or closed cells in the elastomer film. The material is useful in personal care products such as diapers, feminine care products, child care products, incontinence products and health care products where such properties are desirable for attributes such as comfort, body shaping, conformance, dryness and the like.

According to a method of the present invention, an elastomer polymer material is mixed with a cell opening agent. The mixture is extruded through a film extrusion die to form a sheet. Alternatively, a filament-forming die can be used to form filaments. During the extrusion process the cell opening agent decomposes or otherwise physically or chemically reacts to release a gas or other material expanded in volume from its original, pre-extruded form. The gas forms openings or cells within the softened elastomer material. The extruded elastomer material thus has a plurality of open and/or closed cells formed therein which, in the case of open or partially open cells, can transmit air or fluid therethrough. The formed elastomer material can be laminated to other woven or nonwoven facings by known methods to produce a laminate material having desirable breathability and elasticity properties.

The laminate of the present invention can be used in the formation of personal care products, such as, but not limited to, bandages, wound dressings, diapers, training pants, protective swimming undergarments for children, incontinence garments, panty shields or liners, or perspiration shields. The laminate can also be used in the formation of disposable protective apparel, such as, but not limited to, surgical gown or industrial workwear.

BRIEF DESCRIPTION OF THE DRAWINGS

The invention is illustrated in the drawings in which like reference characters designate the same or similar parts throughout the figures of which.

DESCRIPTION OF THE INVENTION

Definitions

Figure 1:
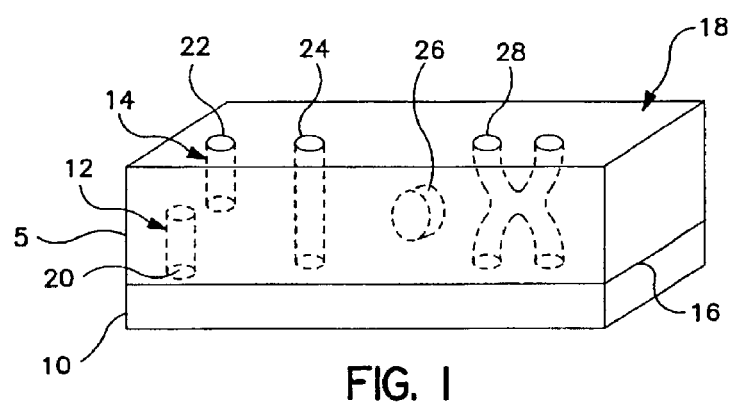
FIG. 1 is a schematic cross-sectional view of a section of an elastomer film laminated to a facing according to the present invention and showing the various types of cells and apertures that can be formed.

As used in the present disclosure, the term "nonwoven" fabric or web means a web having a structure of individual fibers or threads which are interlaid, but not in a regularly repeating pattern as in a meshed or knitted fabric. Nonwoven fabrics or webs have been formed by many processes such as, for example, meltblown, spunbond, hydroentanglement, air-laid, bonded carded web and other processes.

As used in the present disclosure, the term "spunbond fibers" refers to small diameter fibers of polymeric material, which may or may not be molecularly oriented. Spunbond fibers may be formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, and U.S. Pat. No. 5,382,400 to Pike et al. Spunbond fibers are generally not tacky when they are deposited onto a collecting surface and are generally continuous. Spunbond fibers are often about 10 microns or greater in diameter. However, microfiber spunbond may be achieved by various methods including, but not limited to, those described in commonly assigned U.S. application Ser. No. 08/756,426 filed Nov. 26, 1996, now a continuation patent application filed Apr. 30, 1998, now U.S. Pat. No. 6,200,669 by Mormon et al. and U.S. Pat. No. 5,759,926 to Pike et al.

As used in the present disclosure, the term "meltblown fibers" means fibers of polymeric material which are generally formed by extruding a molten thermoplastic or thermosetting (i.e., crosslinkable reagents or post-crosslinkable polymers) to form an elastic material through a plurality of fine, usually circular, die capillaries as molten threads or filaments into converging high velocity, usually hot, gas (e.g., air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers, which can include microfiber webs. Such a process is disclosed, for example, in U.S. Pat. No. 3,849,241 to Butin et al. Meltblown fibers may be continuous or discontinuous and are generally tacky when deposited onto a collecting surface.

As used in the present disclosure, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used in the present disclosure, the term "polymer" generally includes but is not limited to, homopolymers, copolymers, such as for example, block, graft, random and alternating copolymers, terpolymers, etc., and blends and modifications thereof. Furthermore, unless otherwise specifically limited, the term "polymer" includes all possible spatial configurations of the molecule. These configurations include, but are not limited to isotactic, syndiotactic and random symmetries.

As used in the present disclosure, the term "machine direction" or MD means the length of a fabric in the direction in which it is produced. The term "cross machine direction" or CD means the width of fabric, i.e., a direction generally perpendicular to the MD.

As used in the present disclosure, the term "extensible" means elongatable or stretchable in at least one direction.

As used in the present disclosure the term "recover" refers to a retraction of a stretched material upon removal of a biasing force following stretching of the material by application of the biasing force. For example, if a material having a relaxed, unbiased length ($L_0$) of 1 inch (2.54 cm) was stretched to a length of 1.5 inches (3.81 cm) the material would have undergone 150% elongation ($L*100/L_0=$ 1.5*100/1) where elongation is defined as the stretched length (L) divided by the unbiased length ($L_0$). If this exemplary stretched material contracted, that is, recovered to a length of 1.1 inches (2.79 cm) after release of the biasing and stretching force, the material would have recovered 80 percent (0.4 inch, 1.02 cm) of its elongation.

As used in the present disclosure, the term "elastic" means a material which, upon application of a biasing force, is stretchable, that is extensible, to a biased length which is at least 200% of its relaxed unbiased length, and which will retract at least 75% of its elongation upon release of the elongating force. A hypothetical example would be a sample of a material 1 inch (2.54 cm) in length which is stretched to at least 2.0 inches (5.08 cm) and which, upon release of the biasing force, will retract to at least 1.75 inches (4.45 cm) or lesser with an ideally elastic material retracting to the unbiased length of 1 inch (2.54 cm).

As used in the present disclosure, the term "inelastic" or "nonelastic" refers to any material which does not fall within the definition of "elastic" above.

As used in the present disclosure, the term "personal care product" means those products or articles, or components of products or articles, which absorb fluids and semi-fluids, such as bodily waste, but where breathability and air exchange is important. Such products include, but are not limited to, diapers, training pants, absorbent underpants, adult incontinence products, feminine hygiene products, bandages, dressings and like performing products.

As used in the present disclosure, the terms and their forms including: "aperture", "cell", "pore", hole, and "micropore" are used interchangeably and generally refer to an opening at least partially within a structure, such as, but not limited to, a sheet of material. The opening can extend from the surface inward, or from one surface completely through the structure and extend out another surface, i.e., an open cell, or the opening can be completely within the structure, i.e., a closed cell not open to the external surface. The path or shape of the aperture can be straight, tortuous, curved, generally circular, oblong, spherical, intertwined, interconnected or any other shape or relationship of shapes. See FIG. 1.

As used in the present disclosure, the term "layer" will generally refer to a single piece or sheet of material, but the same term should also be construed to mean multiple sheets or plies of material which, together, form one or more of the "layers" described herein.

As used in the present disclosure, the term "stretch bonded" refers to an elastic member being bonded to another member while the elastic member is extended at least about 25 percent of its relaxed length.

As used in the present disclosure, the term "stretch bonded laminates" refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, by example, in U.S. Pat. No. 4,720,415 to Vander Wielen et al., in which multiple layers of the same elastomeric polymer produced from multiple banks of extruders are used. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and 4,655,760 to Morman et al.

As used in the present disclosure, the term "neck bonded" refers to an elastic member being bonded to a non-elastic member while the non-elastic is extended in one direction to be necked in a perpendicular direction.

As used in the present disclosure, the term "neck bonded laminate" refers to a composite material having at least two layers in which one layer is a necked, non-elastic layer and the other layer is an elastic layer. The layers are joined together when the non-elastic layer is in a necked condition. Examples of neck-bonded laminates are such as those described in U.S. Pat. Nos. 5,226,992; 4,981,747; 4,965,122; and 5,336,545 to Morman.

As used in the present disclosure, the term "breathable" refers to a material which is permeable to water vapor having a minimum water vapor transmission rate (WVTR) of about 300 g/m$^2$/24 hours. The WVTR of a fabric, in one aspect, gives an indication of how comfortable a fabric would be to wear. WVTR is measured as described in the Examples hereinbelow and the results are reported in g/m$^2$/24 hours. However, often applications of breathable barriers desirably have higher WVTR measurements and breathable barriers of the present invention can have WVTR measurements exceeding 500 g/m$^2$/24 hours, 800 g/m$^2$/34 hours, 1500 g/m$^2$/24 hours or even exceeding 20,000 g/m$^2$/24 hours.

DETAILED DESCRIPTION OF THE PREFERRED EMBODIMENTS

The present invention provides a breathable elastomeric laminate material comprised of at least one layer of a woven or nonwoven material and at least one layer of a cellular elastomer film or cellular fibrous material. If desired, additional extensible layers may be attached to the laminate as, for example, a second extensible fibrous woven or nonwoven facing layer on a surface of the elastic film layer which is opposed to the extensible facing layer. The film layer has been processed to create apertures or cells using a novel process, as described hereinbelow.

The film layer is composed of an elastomeric resin. Useful elastomeric resins include, but are not limited to, block copolymers having the general formula A-B-A' or A-B, where A and A' are each a thermoplastic polymer endblock which contains a styrenic moiety such as a poly(vinyl arene) and where B is an elastomeric or rubber polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated (A-B)$_m$—X, wherein X is a polyfunctional atom or molecule and in which each (A-B)$_m$-radiates from X in a way that A is an endblock. In the radial block copolymer, X may be an organic or inorganic polyfunctional atom or molecule and m is an integer having the same value as the functional group originally present in X. It is usually at least 3, and is frequently 4 'or 5, but not limited thereto. Thus, in the present invention, the expression "block copolymer," and particularly A-B-A' and A-B block copolymer, is intended to embrace all block copolymers having such rubbery blocks and thermoplastic blocks as discussed above, which can be extruded, and without limitation as to the number of blocks. The polymer may be formed from, for example, elastomeric polystyrene/poly(ethylene-butylene)/polystyrene block copolymers. Commercial examples of such elastomeric copolymers are, for example, those known as KRATON® materials which are available from Shell Chemical Company of Houston, Tex. KRATON® block copolymers are available in several different formulations, a number of which are identified in U.S. Pat. Nos. 4,663,220 and 5,304,599. Also, unsaturated polymers can be used, such as, but not limited to, styrene-butadiene-styrene (SBS), styrene-isoprene-styrene (SIS), and the like.

Polymers composed of an elastomeric A-B-A-B tetrablock copolymer may also be used in the practice of this invention as the elastic layer. Such polymers are discussed in U.S. Pat. No. 5,332,613 to Taylor et al. In such polymers, A is a thermoplastic polymer block and B is an isoprene monomer unit hydrogenated to a poly(ethylene-propylene) monomer unit An example of such a tetrablock copolymer is a styrene-poly(ethylene-propylene)-styrene-poly(ethylene-propylene) or SEPSEP elastomeric block copolymer available under the KRATON® trademark.

Other exemplary elastomeric materials which may be used include polyurethane (such as -(A-B)-$_n$ where A is a hard block and B is a rubber block) elastomeric materials such as, for example, those available under the trademark ESTANE® from B. F. Goodrich & Co. or MORTHANE® from Morton Thiokol Corp., polyetherester elastomeric materials such as, for example, those available under the trade designation HYTREL® from E. I. du Pont de Nemours & Company of Wilmington, Del., and those known as ARNITEL®, formerly available from Akzo Plastics of Arnhem, Holland and now available from DSM of Sittard, Holland.

The thermoplastic copolyetherester elastomers include copolyetheresters having the general formula:

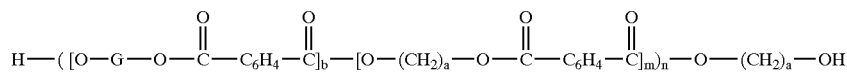

where "G" is selected from the group consisting of poly(oxyethylene)-alpha, omega-diol, poly(oxypropylene)-alpha,omega-diol, poly(oxytetra-methylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117. Another suitable material is a polyetherester block amide copolymer having the formula:

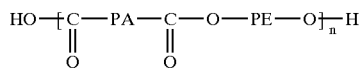

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235° C./1 Kg load); a modulus of elasticity in flexure of from about 20 MPa to about 200 MPa, as measured in accordance with ASTM D-790; a tensile strength at break of from about 29 MPa to about 33 MPa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235° C./1 Kg load); a modulus of elasticity in flexure of about 29.50 MPa, as measured in accordance with ASTM D-790; a tensile strength at break of about 29 MPa, as measured in accordance with ASTM D-639; and an elongation at break of about 650 percent as measured in accordance with ASTM D-638. Such materials are available in various grades under the trade designation PEBAX® from ELF Atochem Inc., Philadelphia, Pa. Examples of the use of such polymers may be found in U.S. Pat. Nos. 4,724,184; 4,820,572; and 4,923,742, both to Killian et. al. and assigned to the same assignee as this invention.

Elastomeric polymers also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

The nonwoven layer is preferably formed by a spunbond or meltblown process, although other processes are possible including, but not limited to, hydroentangling, airlaid, bonded carded webs, flocced structures, needlepunched webs, spunlace, and the like. The spunbond material is comprised of a polyolefin selected from the group consisting of polypropylenes, polyethylenes, and copolymers of propylene and ethylene suitable for spunbond processing. A preferred polypropylene is available as Exxon® PD 3445 polypropylene (hereinafter sometimes referred to as "PP"), available from Exxon Chemical Company, of Houston, Tex. It was also found that blending the Exxon® PD 3445 with a lower viscosity polypropylene typically used for meltblown applications, such as Montell® PF 015 polypropylene (hereinafter sometimes referred to as "Montell® PD 015") available from Montell Chemical of Wilmington, Del., where the Exxon® PD 3445 was present in a range of approximately 50–100%, more preferably approximately 66%, provided an acceptable mix. It was found that 100% Exxon® PD 3445 provided a higher quality result than using a blend of polypropylene resins of narrow molecular weight distributions with lower melt viscosities; e.g., the melt flow (at 230° C.) is greater than about 35 grams/10 minutes. It is to be understood, however, that for certain purposes such a blend can be employed. Where a copolymer of propylene and ethylene is used, the ethylene content is present in a concentration of approximately 7% or less with approximately 93% or more of propylene. It is to be understood that bicomponent, multicomponent, and multiconstituent fibers can be used with the present invention. The nonfilm layer can also be a woven or knitted material. Other suitable elastomeric polymers may also be used to make thermoplastic elastomeric filaments. These include, without limitation, elastomeric (single-site or metallocene catalyzed) polypropylene, polyethylene and other alpha-olefin homopolymers and copolymers, having density less than about 0.89 grams/cc; ethylene vinyl acetate copolymers; and substantially amorphous copolymers and terpolymers of ethylene-propylene, butene-propylene, and ethylene-propylene-butene.

Single-site catalyzed elastomeric polymers (for example, constrained geometry or metallocene-catalyzed elastomeric polymers) are relatively new, and are presently preferred. The single-site process for making polyolefins uses a single-site catalyst which is activated (i.e., ionized) by a co-catalyst.

Polymers produced using single-site catalysts have a narrow molecular weight distribution. "Narrow molecular weight distribution polymer" refers to a polymer that exhibits a molecular weight distribution of less than about 3.5. As is known in the art, the molecular weight distribution of a polymer is the ration of the weight average molecular weight of the polymer to the number average molecular weight of the polymer. Methods of determining molecular weight distribution are described in the Encyclopedia of Polymer Science and Engineering, Volume 3, Pages 299–300 (1985). Polydispersities ($M_w/M_n$) of below 3.5 and even below 2 are possible for single-site produced polymers. These polymers also have a narrow short chain branching distribution when compared to otherwise similar Ziegler-Natta produced polymers.

It is also possible to use a single-site catalyst system to control the isotacticity of the polymer quite closely when stereo selective metallocene catalysts are employed. In fact, polymers have been produced having an isotacticity in excess of 99 percent. It is also possible to produce highly syndiotactic polypropylene using this system.

Commercial production of single-site catalyzed polymers is somewhat limited but growing. Such polymers are available from Exxon Chemical Company of Baytown, Tex. under the trade name EXXPOLL® for polypropylene based polymer and EXACT® for polyethylene based polymers. Dow Chemical Company of Midland, Mich. has polymers commercially available under the name ENGAGE®. These materials are believed to be produced using non-stereo selective single-site catalysts. Exxon generally refers to their single-site catalyst technology as metallocene catalysts, while Dow refers to theirs as "constrained geometry" catalysts under the name INSIGHT® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade.

Regarding single-site catalyzed elastomeric polymers, U.S. Pat. No. 5,204,429 to Kaminsky et al. describes a process which may produce elastic copolymers from cycloolefins and linear olefins using a catalyst which is a stereorigid chiral metallocene transition metal compound and an aluminoxane. The polymerization is carried out in an inert solvent such as an aliphatic or cycloaliphatic hydrocarbon such as toluene. The reaction may also occur in the gas phase using the monomers to be polymerized as the solvent U.S. Pat. Nos. 5,278,272 and 5,272,236, both to Lai et al., assigned to Dow Chemical and entitled "Elastic Substantially Linear Olefin Polymers" describe polymers having particular elastic properties. Dow also commercially produces a line of elastomeric polyolefins under the trade name ENGAGE®.

In a preferred embodiment the cellular film or fibrous woven or nonwoven material of the present invention is made from a polymer resin. Typically, the resin is provided in particulate form, i.e., as a powder, granules or pellets. There may be other materials mixed into the resin for control of other properties, such as a tackifier to increase the bonding capability of the extruded film, or other components to provide easy processability and suitable chemical or physical agents to provide blowing by decomposition, vaporization or in-situ chemical reaction during processing. The resin may also contain other additives that could alter the thermal and other material properties.

The cell opening agent (also referred to as a blowing agent) can be, in its broadest aspect, any material that, when subjected to the film-forming process (e.g., extrusion), produces a gas, preferably, but not mandatorily, inert. The gas creates openings in the film. The cell opening agent can be an azodicarbonamide, such as Celogen® AZN 130 from Uniroyal Chemical Company, Inc., of Middlebury, Conn. The Celogen® product line is a family of chemicals. For further description of this material, see "Celogen® Blowing Agents," RL. Heck, III and W. J. Peascoe, Encyclopedia of Polymer Science and Engineering, Vol. 2, $2^{nd}$ Ed., p. 434 ff. The cell opening agent can also be a fluorocarbon. A further type of cell opening agent are low boiling point solvents (for example, methylene chloride) and water, which create a vapor at the temperature experienced in the die extruder. Celogen® is typically provided as a dispersion or as a powder. The cell opening agent can be provided as a solid, gas, liquid, gel, foam, semi-solid, slurry or other form, depending on the particular characteristics of the specific cell opening agent and the material characteristics desired as an end product.

In an alternative embodiment, the cell opening agent can be selected or modified to produce an active gas (or fluid, solid, particulate or other material) that can be entrapped in cells within the elastomer material during mixing and/or extrusion. The elastomer film material selection can be made to permit release of the gas over a sustained period of time into an environment where the gas can be active and act on a substrate or other substance. It has been shown that high levels of carbon dioxide have an inhibitory effect on yeast filament formation which causes diaper rash. Other yeast, fungus, bacteria, or undesirable microbes may be preventable by the release of an appropriate inhibitory material in gaseous or vapor form from the cells of a film laminated to an extensible material.

Returning to the general discussion of cell opening agents, the polymer resin and cell opening agent are mixed, heated to form a molten resin and transported by the extruder screw to the extruder die entry port. The die is typically heated and the molten resin mixture is extruded or spun into a film sheet or into filaments, fibers or strands by extrusion methods known to those skilled in the art. Extruded film can be prepared through a number of processes such as casting, blowing, and the like. The cell opening agent preferably decomposes in response to elevated temperature, such as that experienced before, during, and/or after the resin exits the film extrusion die bead. It is possible that certain cell opening agents may release gas under other process conditions, such as, but not limited to pH, pressure, light (e.g., ultraviolet, infrared), microwave energy, vibrational energy, electromagnetic energy of other kinds, nuclear energy (e.g., bombardment), and the like. When gas is released or generated, it becomes at least partially trapped within the molten material. If the gas is completely entrapped by the film, it forms cells that are not open to the exterior surface of the material.

In a broad aspect of the present invention, the cell opening agent is capable of undergoing a change of some type, only one of which is decomposition. The change can be a phase transition, decomposition, degradation, other chemical reaction, physical change (e.g., volume increase caused by decreased pressure or increased temperature), energy change, and the like. In one sense, the polymer phase transition matches with the phase transition of the cell opening agent chosen for the particular situation. It is to be understood that these and other structural, chemical, and physical changes are known to those skilled in the art and do not need to be elaborated upon herein.

FIG. 1 is a schematic illustration of the various types of cells and openings which can be formed within an elastomer material 5 that has been laminated to a facing material layer 10. If the gas forms a cell 12 or 14 that extends toward the surfaces 16 or 18, respectively, an opening 20 or 22 is created in the surface of the film. An opening 24 extends from one surface 4 to the other surface 6 through the elastomer material 5. Further, the cells can be discrete, as in cell 26 which is completely within the elastomeric material 5 or interconnected, as in cell 28. Other more complex shapes and geometries are possible and are contemplated as being within the scope of the present invention.

It is a feature of the present invention that the quality and quantity of apertures created can be controlled by manipulating the cell opening agent. Most advantageously, aperture size and distribution can be controlled by selection of the cell opening agent and its concentration to provide optimal breathability of the film layer for a given composite material. Other properties that can be controlled include, but are not limited to, the open or closed nature of the apertures, interconnectivity, shape, density, and the like. Breathability is improved by apertures extending completely through the layer and exposed to the surface on both sides.

It is also contemplated by the present invention that the polymer resin and cell opening agent mixture can be extruded, meltblown or otherwise formed into filaments, wherein the gas creates micropore or microcellular apertures in the filaments.

The resulting apertures formed in the elastomer film by this process have a smoother shape than those formed by conventional mechanical aperturing because no puncturing or rupturing of the film normally occurs. Rather, smooth bubbles form within the molten or partially solidified film structure. Such smooth apertures have fewer stress points and are more resistant to tearing, thus creating a material that is stronger and has a higher lineal elastic range because of the greater structural and polymer elasticity. Further advantages of the film layer material produced by the present invention include low density, cost savings, improved breathability and higher WVTR, and greater MD and CD extensibility. A further advantage of a microporous cellular material or its composites is that increased opaqueness can be introduced in an otherwise clear material. The advantage for this material can be improved aesthetics and discretion. More particularly, the appearance of staining such as that associated with feminine care products and infant, child and adult care products could be substantially reduced.

Further, the apertured film layer can be manufactured at a faster rate than by vacuum aperturing or pin aperturing because the additional step of mechanical aperturing is obviated with the present invention. When used as a side panel in training pants and related products, the material exhibits reduced snap back of the elastomer during tearing of the side panels after use, when the pants are being removed.

Alternatively, openings in the material can be created by reaction of suitable reagents which liberate small molecules during in-situ formation. These small molecules must escape from the material and in so doing generate porous pathways. An example of this is the reaction product of an isocyanate with a polyol and water, which produces carbon dioxide, as will be discussed in greater detail hereinbelow. Cellular hollow fiber elastomers can be used as an added cost savings or improvement to current elastomers with similar performance and breathability.

In an alternative embodiment of the present invention, the interior surface of the cells or openings formed can be coated with a material. Such a material can be an indicator material, such as, but not limited to, pH indicators, dyes, liquid crystals, and the like, which can provide a color or other change in response to temperature, acidity/alkalinity, gas production, or other change which occurs during normal usage of a product. Such a material can be useful, particularly in diapers to determine when one has become wet or soiled without extensive examination by prodding or sniffing. In a further alternative embodiment, in the case of a closed cellular elastomer material, a drug, pharmaceutical, medicament, or other material, provided in a solid, semi-solid, liquid, particulate or other form can be encapsulated within cells within the elastomer material and released over time. Such a material can be used in bandages or other wound dressings, transdermal delivery devices and the like.

The cellular material of the present invention can be laminated or otherwise bound to at least one additional layer of material, such as the materials described hereinabove, by techniques known to those skilled in the art.

Figure 2:
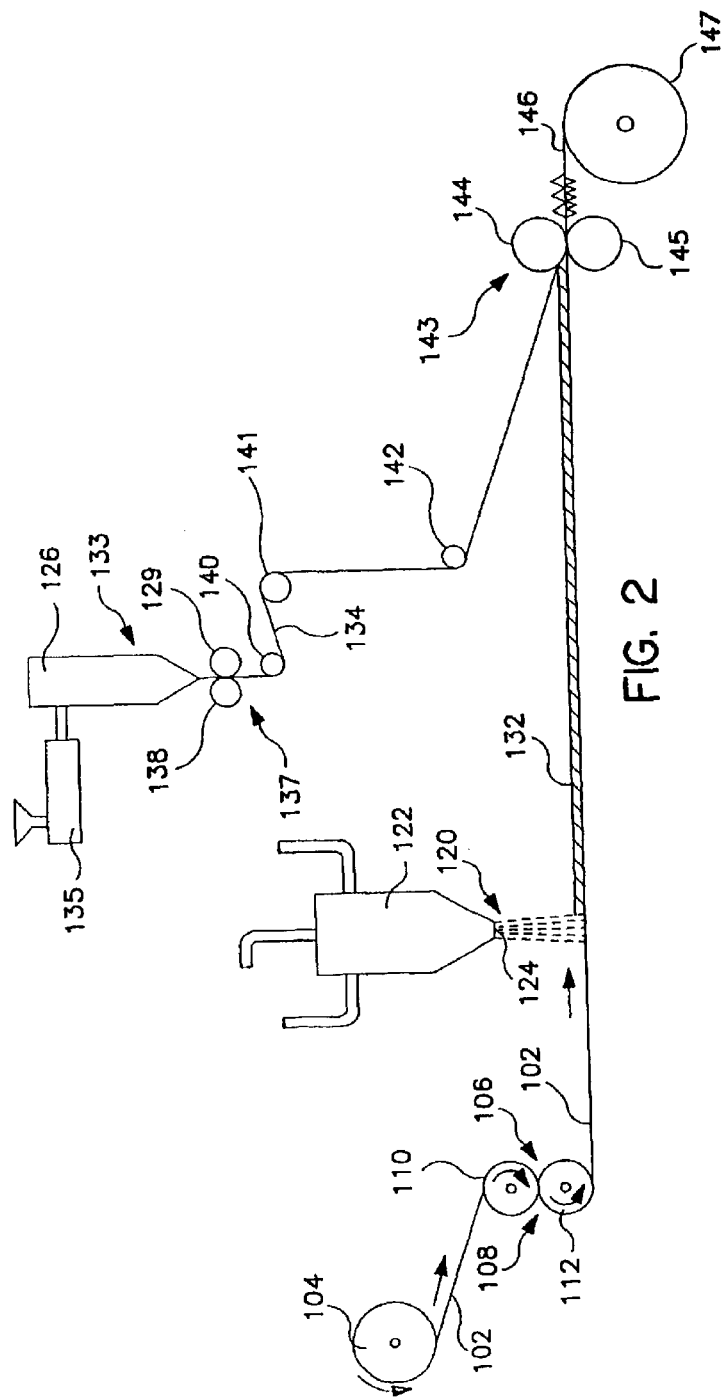
FIG. 2 is a schematic view of a process of forming a composite material containing one facing and an elastomer film layer.

By way of illustration, but not limitation, one such process, shown schematically in FIG. 2, is for the formation of a neck bonded laminate incorporating the elastomer material of the present invention. In such a process a first neckable material 102 is unwound from a supply roll 104. The neckable material 102 then travels in the direction indicated by the arrow associated therewith as the supply roll 104 rotates in the direction of the arrow associated therewith. The neckable material 102 then passes through a nip 106 of an S-roll arrangement 108 formed by the stack rollers 110 and 112. The neckable material 102 may be formed by nonwoven extrusion processes, such as, for example, spunbonding or meltblowing processes, and then passed directly through the nip 106 of the S-roll arrangement 108 without first being stored on a supply roll.

The neckable material 102 then passes through the nip 106 of the S-roll arrangement 108 in a reverse S-wrap path as indicated by the rotation direction arrows associated with the stack rollers 110 and 112. Because the peripheral linear speed of the rollers of the S-roll arrangement 108 is controlled to be lower than the peripheral linear speed of the rollers of the bonder rollers 144 and 145, the neckable material 102 is tensioned so that it necks a desired amount and is maintained in such tensioned, necked condition as the elastic sheet 132 is formed directly on the nonelastic material.

As the necked material 102 passes under a conventional meltblowing process arrangement 122, an elastic sheet 132 of meltblown fibers 120 is formed directly on the necked material 102. The meltblown fibers 120 may include meltblown microfibers. A stream of elastomeric meltblown fibers 120 is directed from the meltblowing process equipment 122 on to the necked material 102 at a high velocity while the fibers are in a softened state so that bonding and/or entangling occurs between the deposited elastomeric sheet of meltblown fibers 132 and the necked material 102.

Generally, the meltblown fibers 120 bond adequately to the necked material when the fibers have an initial high velocity, for example, from about 300 feet (9144 cm) per second to about 1000 feet (30,480 cm) per second.

Additionally, the vertical distance from the forming nozzle 124 of the meltblowing process equipment to the necked material may range from about 4 to about 18 inches (10.16–45.72 cm). For example, the vertical distance may be set at about 12 inches (30.48 cm). The elastic sheet 132 may also be formed by other known extrusion processes.

A film extrusion apparatus 133 produces, in a preferred embodiment, a sheet of cellular elastomer film 134. Initially, an elastomer polymer is mixed with a cell opening agent and introduced into a screw conveyor 135 during which time the polymer mixture is heated to become a molten resin mixture. The mixture is conveyed to a film extrusion die 136 where it is extruded into a film sheet 134. The elastomer film 134 is then passed between a nip arrangement 137 comprised of rollers 138 and 139. The elastomer film 134 is passed through the rollers 140, 141 and 142 (or other number or arrangement). The elastomer film 134 is laminated to the elastic sheet 132 by passing the two sheets through a nip arrangement 143 comprised of bonding rollers 144 and 145, one, both or none of which can be heated. The laminated material 146 is relaxed before it is wound on a takeup roll 147 for storage or additional processing.

Figure 3:
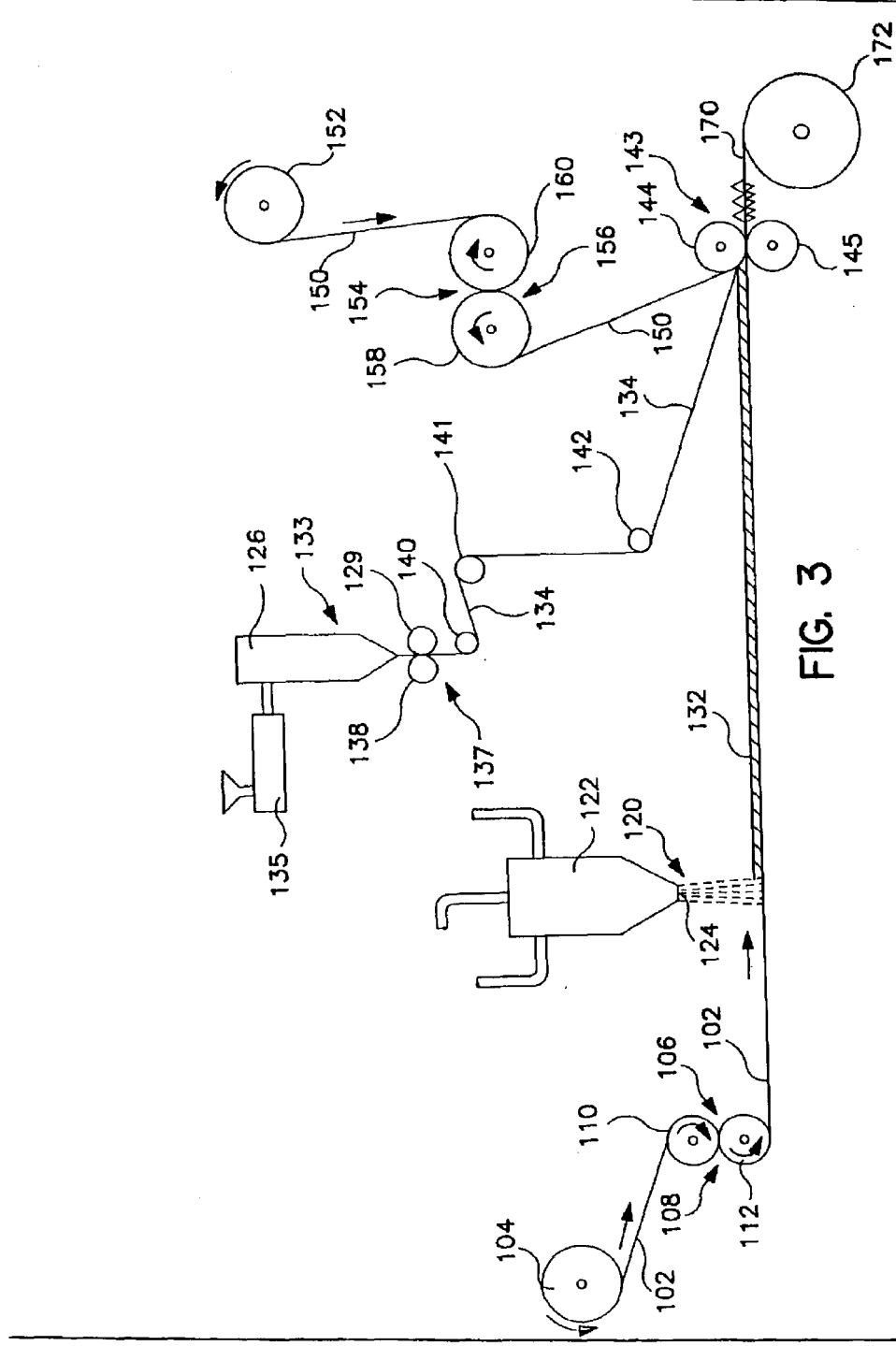
FIG. 3 is a schematic view of a process of forming a composite material containing two facings and an elastomer film layer; and, FIG. 4 is a schematic view of a process of forming a composite elastic material containing at least one anisotropic elastic fibrous web and at least one gatherable layer joined at spaced apart locations.

In an alternative embodiment of the neck bonded laminate process of the present invention, a second neckable material 150 is unwound from a supply roll 152, shown in FIG. 3. The neckable material 150 then travels in the direction indicated by the arrow associated therewith as the supply roll 152 rotates in the direction of the arrow associated therewith. The neckable material 150 then passes through a nip 154 of an S-roll arrangement 156 formed by the stack rollers 158 and 160. Alternatively, the neckable material 150 may be formed by known nonwoven extrusion processes, such as, for example, known spunbonding or known meltblowing processes, and then passed directly through the nip 154 of the S-roll arrangement 156 without first being stored on a supply roll 152.

The neckable material 150 passes through the nip 154 of the S-roll arrangement 156 in a reverse S-wrap path as indicated by the rotation direction arrows associated with the stack rollers 158 and 160. Because the peripheral linear speed of the rollers of the S-roll arrangement 156 is controlled to be less than the peripheral linear speed of the rollers of the bonder roller arrangement 143, the neckable material 150 is tensioned so that it necks a desired amount and is maintained in such tensioned, necked condition as it is overlaid on the elastic sheet 132, the necked material 102 and the elastomeric sheet 134. The four layers are passed through the nip of the bonder roller arrangement 143 to produce a composite elastic necked bonded material 170 which is relaxed and wound on a wind-up roll 172. The bonder roller arrangement 143 may be a patterned calender roller arranged with a smooth anvil roller. Alternatively, a smooth calender roller may be used. One or both of the calender roller and the anvil roller may be heated and the pressure between these two rollers may be adjusted by well-known means to provide the desired temperature and bonding pressure. Other methods may be used to join the layers, such as, for example, adhesives, ultrasonic welding, laser beams, and/or high energy electron beams. The bond surface area on the composite elastic necked bonded laminate may approach about 100 percent and still provide a material with predictable stretch properties.

Figure 4:
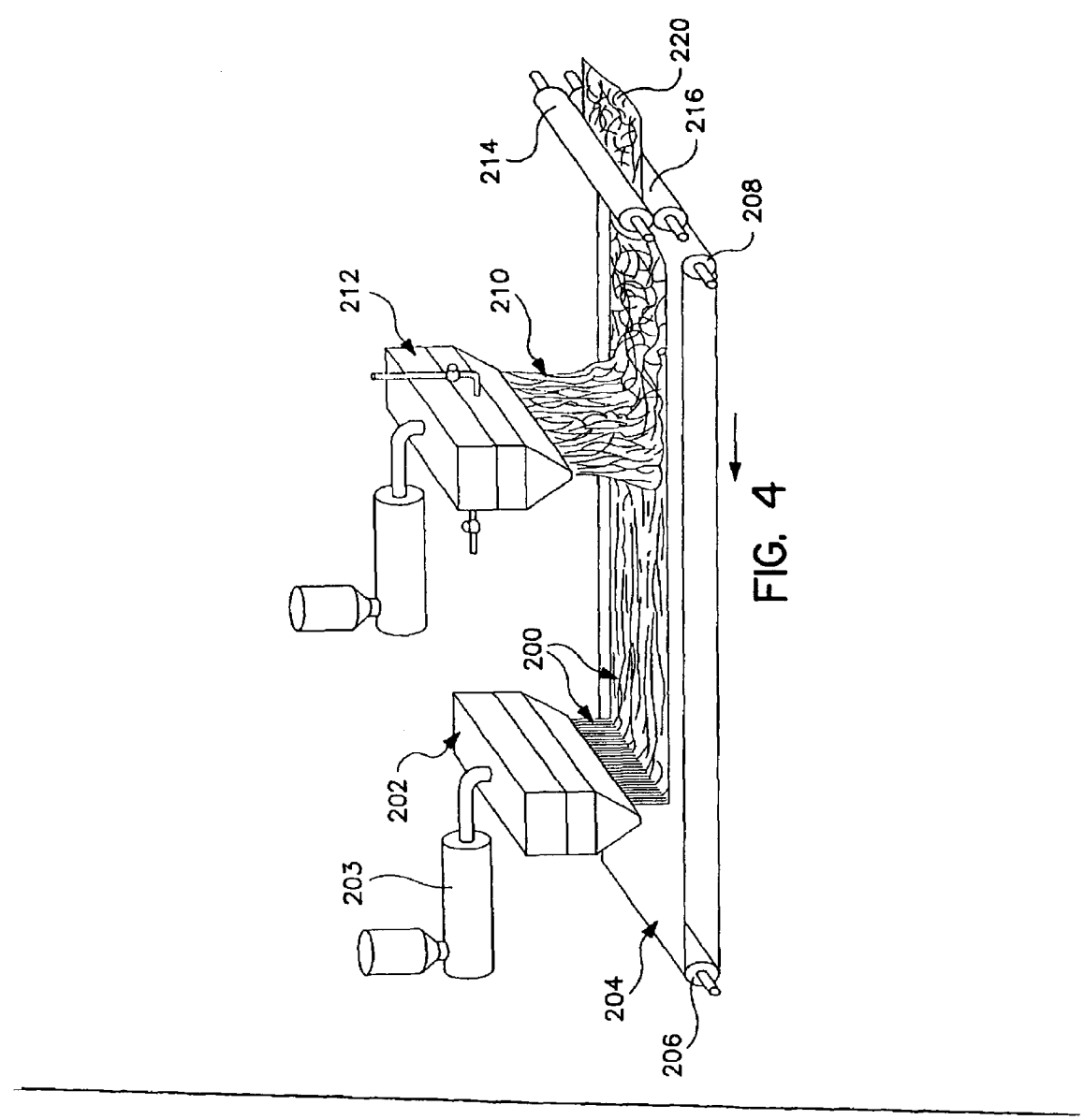

The elastomer film of the present invention can also be used in a process to form a composite elastic material containing at least one anisotropic elastic fibrous web and at least one gatherable layer joined at spaced apart locations. Such a material is disclosed in U.S. Pat. No. 5,385,775 to Wright. Wright discloses a process, shown in FIG. 4, in which, briefly summarized, a layer of elastomeric filaments 200 is extruded from a polymer resin being conveyed to a continuous filament extrusion die 202 via an extruder 203 and deposited onto a foraminous collecting surface 204 which is an endless belt conventionally driven by rollers 206 and 208. The elastomeric filaments 200 are deposited in substantially parallel alignment on the surface of the belt 204, which rotates in the direction of the arrow shown associated therewith. In accordance with the present invention a cell opening agent can be added to the extrusion mix prior to conveyance into the extrusion die 202. The elastomeric filaments 200 will contain cells when extruded Meltblown fibers 210 are formed by meltblowing die apparatus 212 and deposited onto the elastomeric filaments 200. The two layers can be calendered by passing the layers through nip arrangement comprised of rollers 214 and 216 under sufficient pressure (and temperature, if desired) to cause permanent autogenous bonding between the elastomeric filaments 200 and the elastomeric meltblown fibers 210. Further details concerning this process are disclosed in U.S. Pat. No. 5,385,775 issued to Wright. At least one layer of the bonded laminate product 220 of this process can in turn be laminated to at least one layer of an elastomeric material of the present invention to form a composite structure. The resulting laminate composite material demonstrates desirable elastic properties as well as breathability and barrier characteristics properties of materials known in the art using polyolefins, but have the stretch characteristics of elastomer materials.

Conventional drive means and other conventional devices which may be utilized in conjunction with the apparatus described above are well known to those of ordinary skill in the art and, for purposes of clarity have not been illustrated.

A cellular elastomeric film or fibrous nowoven or woven material can be stretched either cross-directionally or in the machine direction and then laminated to a second material such as a film, foam, woven, nonwoven or the like. Upon lamination, the elastic material will retract and permit the material to gather and form a micro or macrotopography. The extent to which this occurs is a direct function of the material properties of each layer and the bonding pattern.

The cell opening agent can alternatively be a mixture of components, as discussed hereinabove, such as the reaction of an isocyanate and a polyol with water. The following presents a method and an apparatus for producing a material incorporating such an agent.

Figure 5:
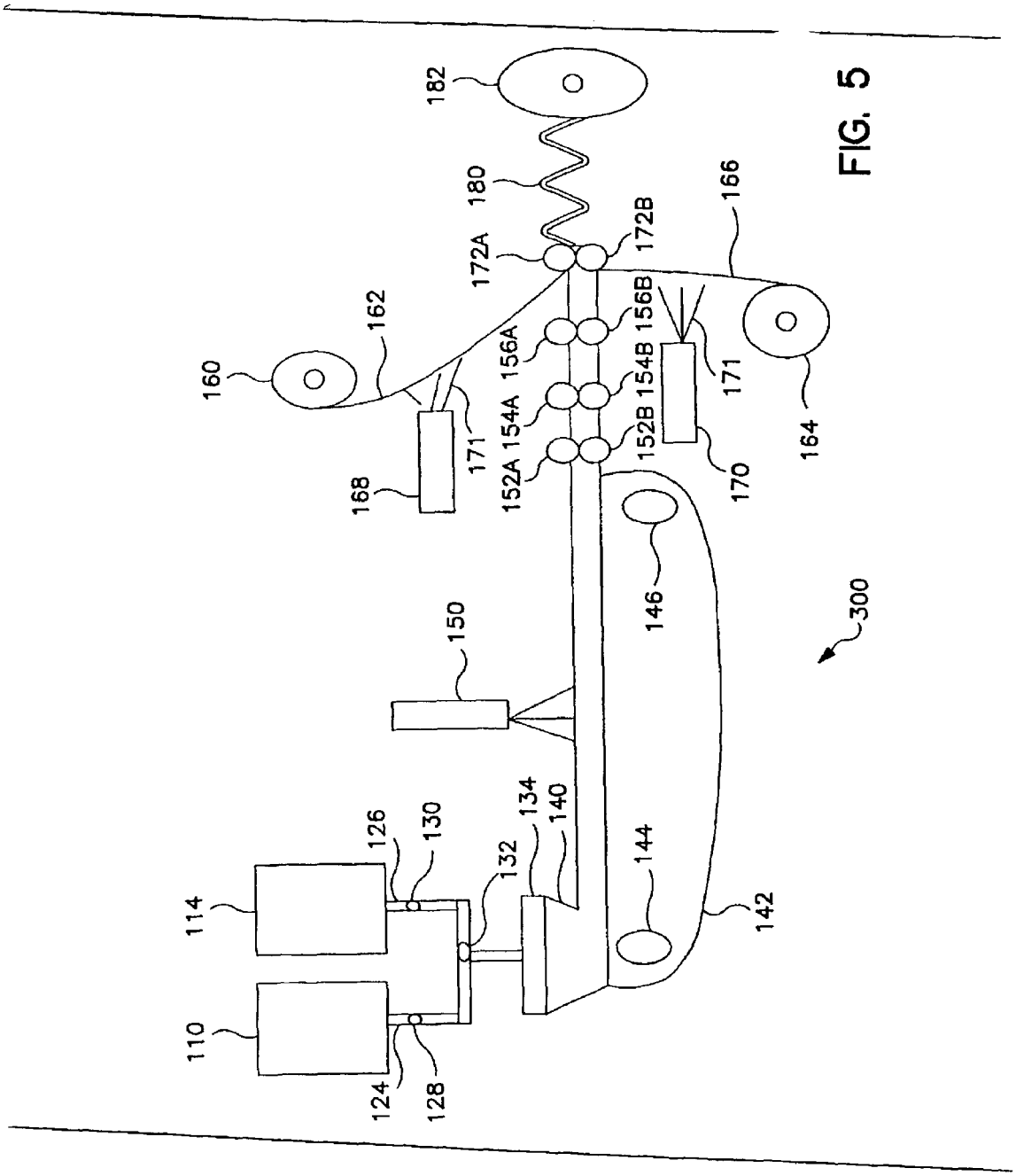
FIG. 5 is a schematic view of a process of forming a composite elastic material using the reaction of a mixture of an isocyanate and polyol with water as the cell opening agent.

FIG. 5 shows an apparatus 300 for forming a composite material using a cell opening agent comprising a mixture of an isocyanate and a polyol. A hopper 110 receives and holds an isocyanate 112. The isocyanate 112 can be, but is not limited to, aliphatic, cyclic saturated, prepolymers, diphenylmethane-4,4'-diisocyanate (MPI) and toluene diisocyanate (TDI), mixtures of the foregoing and the like. Aliphatic isocyanates are preferred because they are less susceptible to discoloration. The hopper 114 receives and holds a polyol 116. The polyol 116 can be, but is not limited to, a polyether, polyester, mixtures thereof and the like. The tackiness of the film formed therefrom can be adjusted by adjusting the monol, diol or triol component of the polyol 116. To the hopper 114 can also be added a catalyst 118, such as, but not limited to, tin, stannous octarate, Dabco 33LV (available from Air Products Co., Wayne, Pa.), one of the NIAX family of materials (available from Union Carbide, New York, N.Y.), mixtures thereof or the like. To the hopper 114 can optionally be added one or more additives 120, such as, but not limited to, brighteners, crosslinking agents (including, but not limited to, diethanolamine, triethanolamine, glycerine and the like), ultraviolet light sensitizers, opaquing agents, mixtures thereof, and the like. Water 122 is also added. The materials in the hoppers 110 and 114 flows through conduits 124 and 126 and through valves 128 and 130, respectively, and to a mixhead 132 (for example, an impingement mixhead). The mixhead 132 dispenses the mixture product to a die head dispenser 134 which extrudes the mixture into a foam 140 containing microcells (not shown) and onto a foraminous forming wire 142, which is in an endless loop and travels on two rollers 144 and 146. The isocyanate 112 reacts with the polyol 116 and the water 122 to form polyurethane/polyurea; a byproduct of this reaction is carbon dioxide gas, which forms within the foam, thus creating a cellular structure.

The foam 140 is subjected (if necessary) to hot air curing by a hot air source 150, which can be a forced air dryer, microwave, infrared heat, convection, an oven, other heat source, ultraviolet light curing or other curing process known to those skilled in the art. The cured foam 140 is now a film 140. Niprolls 152A and B, 154A and B, and 156A and B in combination stretch the film 140 to retain film width while minimizing necking. The niprolls can be adjusted to different speeds to control stretch characteristics. It is to be understood that fewer or more pairs of niprolls can be used to impart desirable stretch characteristics while minimizing necking.

A supply roll 160 supplies an non-extensible facing 162, as described hereinabove, and, a supply roll 164 supplies a second non-extensible facing 166. As the facings 162 and 166 are unwound sprayers 168 and 170 spray an adhesive 171 onto the respective facings to facilitate lamination to the film 140. Any commonly used adhesive can be utilized. An example of an adhesive is Findley 2525A, available from AtoFindley, Inc., Wauwatosa, Wis., which is a urethane type adhesive. The film 140 is then sandwiched between the facings 162 and 166 and the three layers are passed between at least one set of niprolls 172A and B (more than one set of niprolls can be used) to form a laminate material 180, which is relaxed and wound on a takeup roll 182 or transferred for post-formation treatment or processing. It is to be understood that one facing layer can be laminated to the film, or, that multiple facings and film layers can be laminated together to form a thicker material.

Generally stated, the present invention also provides a method of forming cells in a film laminate and controlling pore size distribution in an elastomeric material, comprising: (a) providing an elastomeric polymeric material; (b) providing a cell opening agent; (c) mixing said polymeric material and said cell opening agent to form a mixture; and, (d) extruding said mixture through an extrusion die into a sheet such that apertures will form at least partially within said sheet from the decomposition of said cell opening agent into a gas.

The composite material of the present invention can be used as a component in personal care articles, such as, but not limited to, diapers, training pants, absorbent underpants, adult incontinence products, feminine hygiene products and like performing products. The material can also be used in a composite as a stretchable top sheet for use in management of viscous fluids (e.g., diapers, feminine care products and the like), where a dual layer composite consisting of a top film layer and a bottom layer in which the top layer consists of at least 10% elastic thermoplastic matter that has been apertured according to the present invention. As a stretchable top sheet material or transfer delay material, area containing the cells may range from about 10% to about 50% of the total material. Aperture diameter can be in the range of about 400 microns to about 3000 microns. The material of the present invention can also be used in woven, fiber or ribbon materials with a laminated spunbond layer to produce headbands, waistbands, automotive knitted fabrics, carpet backings and the like. The apertured film layer can be used itself as an elastic foam in a diaper waistband or other compressible structure.

The material of the present invention can be used as or in the outer cover or side panels of diapers, training pants and children's' protective undergarments for swimming. The material contains a particular sheen which is reminiscent of high quality elastic material used in adult bathing suit applications. The high recovery attributed to the elastic material can assist in preventing leakage of urine or feces from such products into the surrounding pool environment. The materials can also provide the look and feel of real bathing suits rather than materials that resemble briefs or diapers which have been colored to look aesthetically pleasing.

Alternatively, the stretchable cellular material or composite of the present invention can be utilized as a topsheet material for personal care products to achieve improved fit and body conformance to permit direct pathways for fluid passage. Additionally, the apertures can be tailored such that upon interaction with compressive or tensile forces such as those imposed by the legs and body during normal wear, the apertures change size and/or shape. This change in size could facilitate the absorption or intake or menstrual fluid which varies in elasticity and viscosity while reducing the chances of fluid rewet. For instance, it is well known that large pores or apertures can improve intake rates as well as permit the passage of highly elastic or viscous components. However, large apertures also permit the rewet of lower elasticity fluids. Thus, a cellular elastic film could permit the intake of both types of a range of menstrual fluids while reducing rewet. Alternatively, the cellular material of the present invention, either in film or fibrous form could be utilized as a single material for use as spunbond facings in diapers and other personal care products to promote both breathability and conformability.

The cellular material of the present invention as well as its composites could be utilized for health care and wound care applications where properties such as stretch and breathability are important in covering wounds but allowing interaction and exchange with air and environment. These cellular materials and their composites are also valuable for apparel and clothing where both comfort, breathability, and fit are deemed as important. The specific characteristics of the cellular materials could be specified based on the end use application.

The invention will be further described in connection with the following Examples, which are set forth for purposes of illustration only. Parts and percentages appearing in such Examples are by weight unless otherwise stipulated.

Test Procedures

Air Permeability

This test is used to determine the rate of air-flow through a known dry specimen area. The higher the result reading, the more open the material is, thus allowing more air to pass through the material. The air-flow though the test specimen is measured with a variable orifice. The air permeability of the test specimen is determined from the pressure drop across this orifice, and is digitally displayed in the selected unit of measure for direct reading. The air permeability tester used was the Textest™ FX 3300 available from Schmid Corporation of Spartanburg, S.C. The tests were conducted in a standard laboratory atmosphere of 23±1° C. (73.4±1.8° F.) and 50±2% relative humidity. The test specimen is used as is or cut to a size so that the specimen extends beyond the clamping area.

Tension Set

In this intermittent stress-elongation experiment, a sample is stretched to a predetermined elongation, released and then stretched to a next greater degree of elongation and so on. The remaining strain at a given time after the removal of the applied stress is then measured. The tension set is a measure of the irreversibility of deformation.

Water Vapor Transmission Rate (WVTR)—Celgard® Test

This test is used to determine the steady state water vapor transmission rate ("WVTR") through various materials, including nonwoven, microporous film, solid film materials, and the like. The material to be evaluated is sealed to the top of a cup of water and placed in a temperature-controlled environment. Evaporation of the water in the cup results in a relatively higher water vapor pressure inside the cup than the vapor pressure of the environment outside of the cup. This difference in vapor pressure causes the vapor inside the cup to flow through the test material to the outside of the cup. The rate of this flow is dependent upon the permeability of the test material sealed to the top of the cup. The difference between the beginning and ending cup weights is used to calculate the water vapor transmission rate. The WVTR for the sample materials was calculated in accordance with the following method: Circular samples measuring 3 inches (7.62 cm) in diameter were cut from each of the test materials and the control which was a piece of Celgard 2500 from the Hoescht Celanese Corporation of Summerville, N.J. Celgard 2500 film is a microporous polypropylene film. The test dish was a #60-1 Vapometer pan distributed by Thwing-Albert Instrument Company of Philadelphia, Pa. One hundred milliliters of water was poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 cm diameter circle, having an exposed area of approximately 33.17 cm². The loaded Vapometer cup was weighed and the weight recorded as the "before" weight. The pans were placed in a forced air oven such as, for example, a Blue M Power-O-Matic 60 oven distributed by Blue M Electric Company of Blue Island, Ill. After 24 hours the pans were removed and weighed again (the "after" weight).

The standardized WVTR for the specimens tested was calculated as follows: Calculate the weight lost for each cup. Calculate the specimen base rates as: weight lost specimen cup (g)×7571÷test hours=specimen base rate (g/m²/day). The specimen WVTR was calculated as follows: (specimen base rate)×(5000÷average Celgard® base rate)=WVTR (standardized).

Water Vapor Transmission Rate Through Nonwovens and Plastic Films Using a Guard Film and Vapor Pressure Sensor—INDA Standard Test Method No. IST-70.4-99

At higher water vapor transmission rates, the test procedure standardized by INDA (Association of the Nonwoven Fabrics Industry), number IST-70.4-99, (known to those skilled in the art) which is incorporated by reference herein, may more accurately measure the transmission rate. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the barrier material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W model 100K manufactured Mocon/Modern Controls, Inc, Minneapolis, Minn. A first test is made of the WVTR of the guard film and air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and guard film and stores the value for further use.

The transmission rate of the guard film and air gap is stored in the computer as CalC. The barrier is then sealed in the test cell. Again, water vapor diffuses through the air gap to the guard film and the test barrier and then mixes with a dry gas flow that sweeps the test barrier. Also, again, this mixture is carried to the vapor sensor. The computer then calculates the transmission rate of the combination of the air gap, the guard film, and the test film. This information is then used to calculate the rate at which moisture is transmitted through the material being tested according to the equation:

$$TR^{-1}_{test\ barrier}=TR^{-1}_{test\ barrier,\ guardfilm,\ airgap}-TR^{-1}_{guardfilm,\ airgap}$$

Calculations:

WVTR: The calculation of the WVTR uses the formula:

$$WVTR=F\rho_{sat}(T)RH/Ap_{sat}(T)(1-RH))$$

where:

F=The flow of in cc/min., $\rho_{sat}(T)$=The density of water in saturated air at temperature T, RH=The relative humidity at specified locations in the cell, A=The cross section of area of the cell, and, $p_{sat}(T)$=The saturation vapor pressure of water vapor at temperature T.

Permeance: Calculate sample permeance (if required) using the following relationship:

$$\text{Metric Perms}=(WVTR)/P_w=g/m^2 \text{ per day per mm Hg}$$

where:

WVTR=Specimen water vapor transmission rate, g/m² day, and $P_w$=Water vapor partial pressure gradient across the test specimen, mm Hg.

Calculate the water vapor permeability coefficient (if required) using the following relationship:

$$\text{Permeability}=\text{metric perms}\times t$$

where:

t=the average thickness of the specimen, cm. Note that permeability calculations are meaningful only in cases where the materials have been determined to be homogeneous.

Stress-Elongation

The stress-elongation behavior of these polymers was obtained both at room and body temperatures, using an Instron 1200 or a Sintech 1/S testing frames. Film samples in the shape of a dog bone, approximately 30 mils thick with a center width of 0.5 inches (1.27 cm), were clamped at a grip- to-grip distance of 2 inches (5.08 cm) and were pulled at a cross-head displacement of 2 inches/min (5.08 cm/min). Samples were taken to failure in the room temperature test. In the body temperature measurements, the samples were not taken to failure due to height limitations of the environmental chamber. The load was normalized with respect to the cross-sectional area to obtain stress data. The elongation was calculated from a knowledge of the change in length as well as the original length of the sample. The modulus, which is a measure of the rigidity of the sample, was calculated from the stress and elongation by applying the rubber elasticity theory, as is known to those skilled in the art.

EXAMPLES

General Film Aperturing Procedure Using a Cell Opening Agent

The cellular film samples of the Kraton® polymer (or other material) with and without the additives including the cell opening agent were made on a Haake Rheocord 9000, ¾" screw extruder with a compression ratio of 5:1 and a length:diameter ("L/D") of 32:1. The tip of the screw was fitted with mixing elements to produce a homogeneous mix. The screw had three heating zones: the feed zone (50% of the length of the screw), the compression zone (30% of the length of the screw), and the metering zone (20% of the length of the screw). In addition, the film die was heated. In a typical run which involved a Kraton® polymer containing 0.5% of the cell opener Celogen® AZN 130, the feed zone temperature was at 200° C., the compression zone was set at 210° C., the metering zone was set at 260° C. and the die temperature was set at 230° C. The microcellular film was extruded at a back pressure of 1900–2000 psi at 20 to 30 rpm. These conditions could vary depending on the polymer used. Other conditions can also be chosen depending on the degree of openness and cell size requirements. For example, increasing the speed of the takeup roll results in decreasing the thickness of the film and increasing the average hole diameter. In general, polymer in the form of pellets was blended with cell opener in the dry or slurry form together with other additives, if any, and introduced into the hopper of the extruder and the temperature and RPM of the screw zones and die were adjusted so as to get a cast film of desired properties. The extruded film on exiting the extruder die was passed on to a chill roll and finally to a windup roll which speed was adjusted to get a film with desired open/closed cells, cell size and thickness.

The film material can then be laminated to one or more layers using conventional lamination techniques known to those skilled in the art.

Example 1

1671 g Kratong® 6912, a SEPSEP tetrablock Kratone copolymer.

8.35 g (0.5%) Celogen® AZN 130.

The extruder temperature was set at:

| SET TEMP. (° C.) | 200 | 210 | 260 | 230 |
|---|---|---|---|---|
| ACTUAL TEMP. (° C.) | 209 | 197 | 232 | 250 |

The extruder pressure was 1900–2000 psi. The screw speed was set at 20 rpm.

Example 2

390 g Kraton® 6588.

Example 3

94% Estane® thermoplastic polyurethane 58245 (a polyurethane from B. F. Goodrich)

5% EVA

1% Celogen®.

Example 4

99.5% Estane® 58245

0.5% Celogen®.

Example 5

100% Estane® 58245

TABLE 1

| EXAMPLE NO. | SAMPLE DESCRIPTION | AIR PERMEABILITY 38 $cm^2$ head cfm | WVTR $g/m^2$/24 hrs | ELOGATED LOAD AT BREAK (machine direction) gram | ELONGATION AT BREAK (machine direction) % |
|---|---|---|---|---|---|
| 1 | Kraton ® 6912 + 0.5% Celogen ® | 27 | 2361 | 519 | 607 |
| 2 | Kraton ® 6588 (control) | NO DATA | 34 | 564 | 663 |
| 3 | Estane ® 58245 + 1% Celogen ® + 5% EVA | 14 | 2506 | 1985 | 308 |
| 4 | Estane ® 58245 + 0.5% Celogen ® | 1 | 1175 | 5000 | 579 |
| 5 | Celogen ® 58245 (control) | 1 | 1117 | 5001 | 392 |

TABLE 2

| EXAMPLE NO. | TENSION % SET @ 25% ELONGATION (machine direction) | TENSION % SET @ 50% ELONGATION (machine direction) | TENSION % SET @ 100% ELONGATION (machine direction) | TENSION % SET @ 200% ELONGATION (machine direction) | TENSION % SET @ 300% ELONGATION (machine direction) |
|---|---|---|---|---|---|
| 1 | 2 | 4 | 7 | 11 | 16 |
| 2 | No Data | No Data | No Data | No Data | No Data |
| 3 | 2 | 4 | 7 | 7 | 6 |
| 4 | 2 | 5 | 11 | 8 | 6 |

Tables 1 and 2 show test results of an average of several samples of the given formulation and process. In general, the test results indicate that the elastomer film material produced maintained predictable air permeability, water/moisture barrier (WVTR), extension load at break and extension at break numbers compared to the control samples. For example, the WVTR is increased in Example 1 by adding Celogen® over the control sample (Example 2).

Example 6

Film Laminate

Sample description: SEBS saturated Kraton® G polymer 0.15% Celogen® AZ130 cell opening agent 0.4 osy spunbond facing was used on both sides of the film.

The film had a thickness of 1–4 mm.

The extruder temperature was set at:

| TEMP. (° C.) | 121 | 215.6 | 221.1 |
|---|---|---|---|

The die temperature was 210° C.

TABLE 3

| SAMPLE NO. | INDA IST 70.4–99 test g/m²/24 hrs |
|---|---|
| Mean | 1300 |

Example 7

Laminate

Sample description: SEBS saturated Kraton® G polymer 0.06% Celogen® AZ130 cell opening agent 0.4 osy spunbond facing was used on both sides of the film.

The film was drawn 3.6× and had a thickness of 1–4 mm.

The extruder temperature was set at:

| TEMP. (° C.) | 121 | 215.6 | 221.1 |
|---|---|---|---|

The die temperature was 218.3° C.
The mean INDA IST 70.4-99 test was 133 g/m²/24 hrs.

Example 8

Sample description: SEBS saturated Kraton® G polymer 0.06% Celogen® AZ130 cell opening agent 0.4 osy spunbond facing was used on both sides of the film.

The film was drawn 3.8× and had a thickness of 1–4 mm.

The extruder temperature was set at:

| TEMP. (° C.) | 121 | 215.6 | 221.1 |
|---|---|---|---|

The die temperature was 218.3° C. The takeup speed was higher than in Example 7.

The mean INDA IST 70.4-99 test was 139 g/m²/24 hrs.

As can be seen from the examples, as the concentration of Celogen® is increased, the WVTR breathability increased.

The present invention provides materials which maintain predictable mechanical properties of previously known polymers while decreasing density and increasing WVTR. Olefinic elastomers are not generally inherently breathable to any appreciable extent. Polar elastomers have some breathability. The present invention demonstrates the increased breathability in elastomeric polymers by adding a cell opening agent. As such, these Examples show that the elastomer film material is commercially viable and is favorable compared to conventional apertured film materials, such as polyolefins, but with the elasticity property advantages described above.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications or publications referred to herein are incorporated by reference in their entirety.

What is claimed is:

1. A breathable cellular elastomer filament material having cells created therein by a cell opening agent, said material being essentially free of polystyrene homopolymer and having at least a portion of said cells being closed, said material being breathable and having an elongation at break of from about 300 to about 600 percent.

2. The breathable cellular elastomer filament material of claim 1, wherein said filament material comprises a material selected from the group consisting of a block copolymer having the general formula A-B-A' or A-B, where A and A' are each a thermoplastic polymer endblock which contains a sty nic moiety and where B is an elastomeric or rubber polymer midblock such as a conjugated diene or a lower alkene polymer elastomeric and a A-B-A-B tetrablock copolymer.

3. The breathable cellular elastomer filament material of claim 1, wherein said cell opening agent is an azodicarbonamide, water low boiling point solvent, a fluorocarbon, a mixture of an isocyanate and a polyol or mixtures thereof.

4. The breathable cellular elastomer filament material of claim 1, further comprising at least one layer of an extensible material laminated to said filament material, said filament material having at least one aperture defined therein created by a cell opening agent.

5. The breathable cellular elastomer filament material of claim 4, wherein said cell opening agent is a material capable of forming openings in said filament material.

6. The breathable cellular elastomer filament material of claim 4, wherein said cell opening agent is an azodicarbonamide, water, a low boiling point solvent or the gas liberated by the reaction of a mixture of an isocyanate and a polyol with water.

7. The breathable cellular elastomer filament material of claim 4, wherein said cells are open to said filament material surface, partially open or closed.

8. The breathable cellular elastomer filament material of Claim 4, wherein said composite material has an average water vapor transmission rate of from about 300 to about 20,000 $g/m^2/24$ hours.

9. The breathable cellular elastomer filament material of Claim 4, wherein said composite material has an average water vapor transmission rate as measured by the INDA (Association of the Nonwoven Fabrics Industry) test procedure IST-70.4-99 of from about 300 to about 20,000 $g/m^2/24$ hours.

10. Be material of claim 1, wherein said material has cells created therein by a cell opening agent, at least one of said cells being closed, said closed cells containing a solid, liquid or gas capable of timed release.

11. The breathable cellular elastomer filament material of claim 1, wherein said material is a filament material having cells created there by a cell opening agent, said filament material being at least partiality air permeable, capable of transmitting water vapor therethrough and being elongatable.

12. The breathable cellular elastomer filament material of claim 10, wherein said solid, liquid or gas is released in response to an external stimulus.

13. The breathable cellular elastomer filament material of claim 12, wherein said external stimulus is increased temperature from a user.

14. The breathable cellular elastomer filament material of claim 12, wherein said solid, liquid or gas is active.

15. The breathable cellular elastomer filament material of claim 12, wherein said solid, liquid or gas is capable of inhibiting yeast filament formation.

16. The breathable cellular elastomer filament material of claim 1, further comprising at least one layer of an extensible material laminated to said elastomer material, said elastomer material having at least one aperture defined therein crated by a cell opening agent.

17. The breathable cellular elastomer filament material of claim 4, wherein said filament material is formed by extrusion methods.

18. The breathable cellular elastomer filament material of claim 1, further comprising at least one layer comprised of an extensible material laminated to said elastomeric filament material to form a laminate, said elastomeric filament material having apertures created therein by a cell opening agent, said laminate being formed into a personal care product.

19. The breathable cellular elastomer filament material of claim 18, wherein said laminate has an average water vapor transmission rate as measured by the INDA (Association of the Nonwoven Fabrics industry) test procedure IST-70.4-99 of from about 300 to about 20,000 $g/m^2/24$ hours.

20. The breathable cellular elastomer filament material of claim 18, wherein said laminate is formed into a bandage, a wound dressing, a diaper, an incontinence garment a panty shield or liner, a preparation shield a surgical gown or industrial workwear.

21. A breathable cellular elastomer material having cells created therein by a cell opening agent, said material being at least partially air permeable, capable of transmitting water vapor th through and being elongatable, wherein said material is incorporated into a laminate material produced by a method, comprising:
    a) providing a layer of a spunbond material;
    b) providing a layer of an elastomeric film being essentially free of polystyerene homopolymer and having apertures formed therein by mixing a polymer material with a cell opening agent to form a mixture and extruding said mixture through a die such that apertures are formed therein, said apertures comprising cells, at least a portion of said cells being closed;
    c) stretching said film of step b); and,
    d) laminating said stretched elastomeric film of step b) and said spunbond,
    said breathable cellular elastomer being breathable and having an elongation at break of from about 300 to about 600 percent and being retractable by at least 75% of said elongation.

22. A breathable cellular elastomer material having cells created therein by a cell opening agent, said material being essentially free of polystyrene homopolymer and at least partially air permeable, capable of transmitting water vapor therethrough and being elongatable, wherein said material is incorporated into a laminate material produced by a method, comprising
    a) providing an isocyanate material;
    b) providing a polyol material;
    c) providing a catalyst material;
    d) providing an effective amount of water;
    e) mixing said polyol material, catalyst material and water to form a mixture;
    f) mixing the mixture of step e) with said isocyanate material to form a second mixture;
    g) dispensing said second mixture through a die head onto a surface to form a cellular foam at least a portion of said foam having closed cells;
    h) stretching said from step g) and;
    i) laminating said stretched foam of step h) to at least one layer of a non-extendable material so as to form a breathable elastomeric material;
    said breathable cellular elastomer material being breathable and having an elongation at break of from about 300 to about 600 percent retractable by at least 75% of said elongation.

23. The material of claim 22, further comprising curing said foam.

24. The material of claim 22, further comprising adjusting the polyol functionality to adjust the adhesive level desired.

25. A breathable cellular elastomer filament material having cells created therein by a cell opening agent said material being at least partially air permeable, capable of transmitting water vapor therethrough and being elongatable, wherein having apertures formed therein by a process, comprising:
   a) providing an elastomeric polymer material essentially Se of polystyrene homopolymer;
   b) providing a cell opening material capable of releasing a gas;
   c) said polymer material and said cell opening material to form a mixture; and,
   d) extruding said mixture an extrusion die such that said cell opening material produces a gas whereby apparatus are formed at least partially, within the extruded material, at least a portion of said apertures being closed cells.

26. A laminate material, comprising:
   a) a layer of an elastomer filament material being essentially free of polystyrene homopolymer and having cells created therein by a cell opening agent, at least a portion of said cells being closed, said material being breathable and having an elongation at break of from about 300% to about 600%; and,
   b) at least one layer of a spunbond material laminated to said elastomer filament material.

27. A personal care article, comprising:
   a) a layer of an elastomer filament material being essentially free of polystyrene homopolymer and having cells created then by a cell opening agent, at least a pod of said cells being closed, said material being breathable and having an elongation at break of from about 300% to about 600%; and,
   b) at least one layer of a spunbond material laminated to said elastomer filament material.

28. A, stretchable top sheet for use in an article worn to manage fluids, comprising:
   a) a layer of an elastomer filament material being essentially free of polystyrene homopolymer and having cells created therein by a cell opening agent, at least a portion of said being closed, said material being breathable and having an elongation at break of from about 300% to about 600%; and,
   b) at least one layer of a spunbond material laminated to said elastomer filament material.

* * * * *

UNITED STATES PATENT AND TRADEMARK OFFICE
CERTIFICATE OF CORRECTION

PATENT NO. : 6,855,424 B1 Page 1 of 1
DATED : February 15, 2005
INVENTOR(S) : Oomman Painumoottil Thomas et al.

It is certified that error appears in the above-identified patent and that said Letters Patent is hereby corrected as shown below:

<u>Title page,</u>
Item [75], Inventors, please add the following -- Byron Paul Day --

Signed and Sealed this

Tenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,855,424 B1
DATED : February 15, 2005
INVENTOR(S) : Oomman Painumoottil Thomas et al.

It is certified that error appears in the above-identified patent and that said Letters Patent is hereby corrected as shown below:

Title page,
Item [75], Inventors, please add -- Byron Paul Day --

Signed and Sealed this

Fourteenth Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,855,424 B1
APPLICATION NO. : 09/474043
DATED : February 15, 2005
INVENTOR(S) : Thomas et al.

It is certified that error appears in the above-identified patent and that said Letters Patent is hereby corrected as shown below:

Column 22, line 67, Claim 2, "a sty nic moiety" should read --a styrenic moiety--;
Column 23, line 6, Claim 3, "water low" should read --water, a low--;
Column 23, line 35, Claim 10, "Be material" should read --The material--;
Column 23, line 41, Claim 11, "created there" should read --created therein--;
Column 23, line 60, Claim 16, "therein crated" should read --therein created--;
Column 24, line 10, Claim 20, "garment a panty" should read --garment, a panty--;
Column 24, line 11, Claim 20, "a preparation shield" should read --a perspiration shield--
Column 24, line 16, Claim 21, "vapor th through" should read --vapor therethrough--;
Column 24, line 54, Claim 22, "said from step" should read --said foam of step--;
Column 24, line 56, Claim 22, "of a non-extendable" should read --of a non-extensible;
Column 24, line 60, Claim 22, "percent retractable" should read --percent being retractable--;
Column 25, line 6, Claim 25, "Se of" should read --free of--;
Column 25, line 9, Claim 25, "said polymer" should read --mixing said polymer--;
Column 25, line 11, Claim 25, "mixture an extrusion" should read --mixture through an extrusion--;
Column 25, line 12, Claim 25, "whereby apparatus" should read --whereby apertures--;
Column 26, line 6, Claim 27, "created then by" should read --created therein by--;
Column 26, line 6, Claim 27, "a pod" should read --a portion--.

Signed and Sealed this

Twenty-second Day of May, 2007

JON W. DUDAS
*Director of the United States Patent and Trademark Office*